(12) United States Patent
Bunce

(10) Patent No.: US 8,875,699 B2
(45) Date of Patent: Nov. 4, 2014

(54) INHALER CAP STRAP

(71) Applicant: AstraZeneca AB, Södertalje (SE)

(72) Inventor: Martin Bunce, Marlborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 13/750,082

(22) Filed: Jan. 25, 2013

(65) Prior Publication Data

US 2013/0199525 A1    Aug. 8, 2013

(30) Foreign Application Priority Data

Nov. 17, 2003   (SE) .................................. 0303029-3

(51) Int. Cl.
*A61M 11/00*    (2006.01)
*A61M 15/00*    (2006.01)

(52) U.S. Cl.
CPC ....... *A61M 15/0065* (2013.01); *A61M 15/0025* (2013.01); *A61M 15/0026* (2013.01); *A61M 15/009* (2013.01)
USPC ................................ 128/200.23; 128/200.14

(58) Field of Classification Search
USPC ............. 128/200.14–200.23, 200.11–207.18; 215/2–400; 425/809; 53/287; 292/1–359; 222/1–652; 220/375, 220/345.1, 350, 345.4–345.6
See application file for complete search history.

(56) References Cited

U.S. PATENT DOCUMENTS

| | | | |
|---|---|---|---|
| 2,627,996 A | 2/1953 | Dorner | |
| 3,927,806 A | 12/1975 | Meshberg | |
| 4,637,528 A | 1/1987 | Wachinski | |
| 4,776,486 A | 10/1988 | Mizusawa | |
| 4,848,612 A | 7/1989 | Beck | |
| 5,564,583 A | 10/1996 | Kelley et al. | |
| 5,899,200 A | 5/1999 | McNary | |
| 6,003,205 A | 12/1999 | Dehaven | |
| 6,164,275 A | 12/2000 | Van Iderstine | |
| 6,182,655 B1 | 2/2001 | Keller et al. | |
| 6,357,442 B1 | 3/2002 | Casper et al. | |
| 6,575,330 B2 * | 6/2003 | Rousselet | ........................ 222/1 |
| 6,648,158 B1 | 11/2003 | Lawrence | |
| 6,752,147 B1 | 6/2004 | Goldemann et al. | |
| 2004/0089292 A1 | 5/2004 | Pollet et al. | |

FOREIGN PATENT DOCUMENTS

| | | |
|---|---|---|
| EP | 0476991 | 3/1992 |
| EP | 0808635 | 11/1997 |
| EP | 0652784 | 3/1999 |
| EP | 1632260 | 3/2006 |
| GB | 2272162 | 5/1994 |
| GB | 2364320 | 1/2002 |
| GB | 2364321 | 1/2002 |
| JP | 2002-501791 | 1/2002 |
| PT | 70150 | 10/1979 |
| WO | WO 02/04056 | 1/2002 |
| WO | WO 2005/087299 | 9/2005 |

* cited by examiner

*Primary Examiner* — Rachel Young
(74) *Attorney, Agent, or Firm* — Finnegan, Henderson, Farabow, Garrett & Dunner LLP

(57) ABSTRACT

An inhaler (1) for dispensing doses of medicament from a container under user activation includes a body (7) which includes a mouthpiece (5) through which the medicament is dispensed and a cap (2) which can be place in a position to substantially occlude the mouthpiece (5). The cap (2) is attached to the body (7) by a strap (3) which pivots from the body (7), the cap (2) being arranged to slide on the strap (3) such that the cap (2) must translate away from the mouthpiece (5) prior to the pivoting of the strap (3).

17 Claims, 3 Drawing Sheets

INHALER CAP STRAP

This application is a continuation of U.S. application Ser. No. 10/579,481, filed Apr. 27, 2007, which is a national phase application of PCT/SE2004/001631, filed Nov. 10, 2004, which claims the priority of Swedish Patent Application No. 0303029-3, filed Nov. 17, 2003, all of which are incorporated herein by reference.

The present invention relates to an inhaler for administering medicament by inhalation and in particular to a strap for retaining a nozzle cap.

For some time, inhalers have been known for delivering metered doses of medicament from aerosol canisters through a nozzle. These inhalers vary in complexity and may comprise a single integral moulding or may consist of multiple moulded parts. Inhalers are often constructed of plastic, as this material is strong, light, can be easily moulded and is hygienic. Inhalers are often carried by users in their pockets or bags and such environments are often dirty and dusty. It is known to provide a cap to occlude the nozzle of an inhaler in order to prevent the entrance of dust and dirt, Such caps can be easily lost if they are not retained on the inhaler in some manner. It is possible to attach the cap by means of a flexible strap, which may be made of a rubber material. This complicates the manufacturing process as the remainder of the inhaler is made of plastic. Other means of attaching the strap are unpleasing to the eye. Inhalers are usually coloured to identify the medicament being delivered and it is useful to make sure that the cap and strap are the same colour. It is also useful to make sure that the cap and strap follow the contours of the inhaler in order to prevent dirt getting stuck in gaps and to enable the inhaler to stand upright on the base. When then strap follows the contours of the base of the inhaler it is also possible for the inhaler to stand upright on the base thereby enabling it to be stored in an orientation that enables accurate dosing as known forms of pressurised canister provide accurate dosing when actuated whilst upright.

A preferred form of the present invention will now be described with reference to the accompanying drawings in which FIG. 1 shows a perspective view of an assembled inhaler, which includes a strap according to a preferred form of the present invention, the strap being shown in a closed condition;

Figure 1:
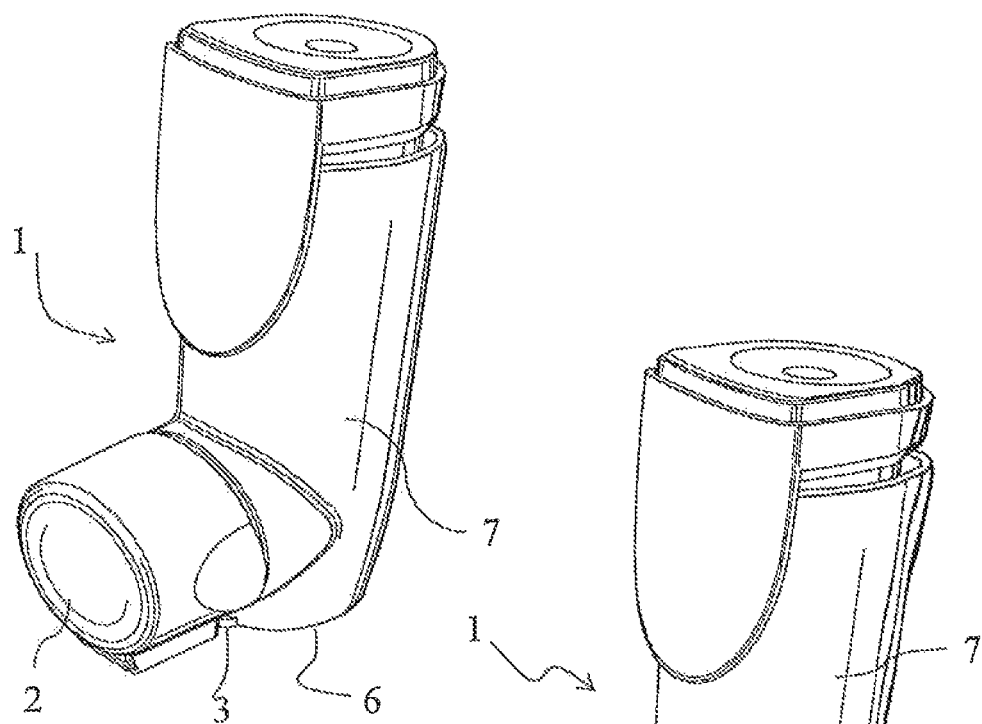
Figure 2:
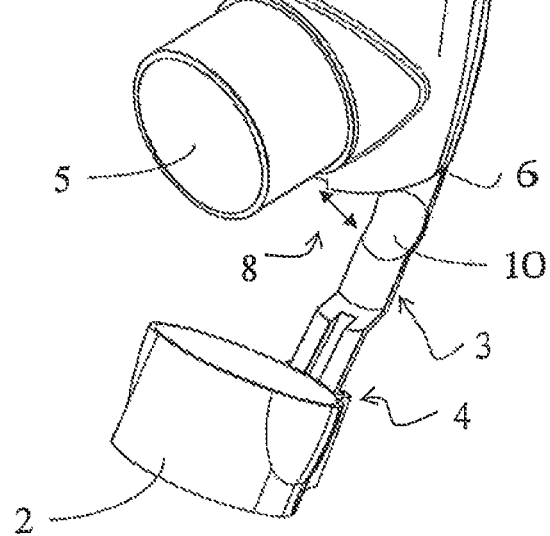
FIG. 2 shows a similar view to that shown in FIG. 1 however in this view the strap is shown in the open condition and is shown in a condition in which it does not underlie the base of the main body of the inhaler.
Figure 3:
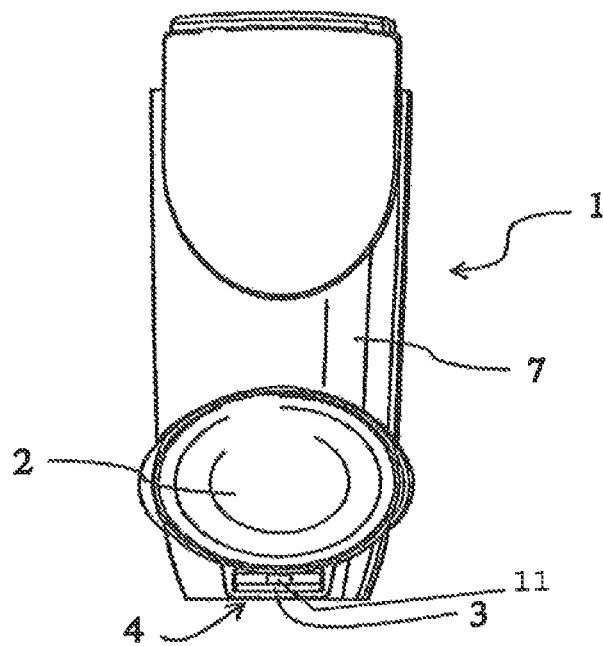
FIG. 3 shows a front view of the mouthpiece of an inhaler, which incorporates a preferred form of the present invention, the portion of the mouthpiece, which is fitted into the main body of the inhaler, is shown in the upper portion of this view.
Figure 4:
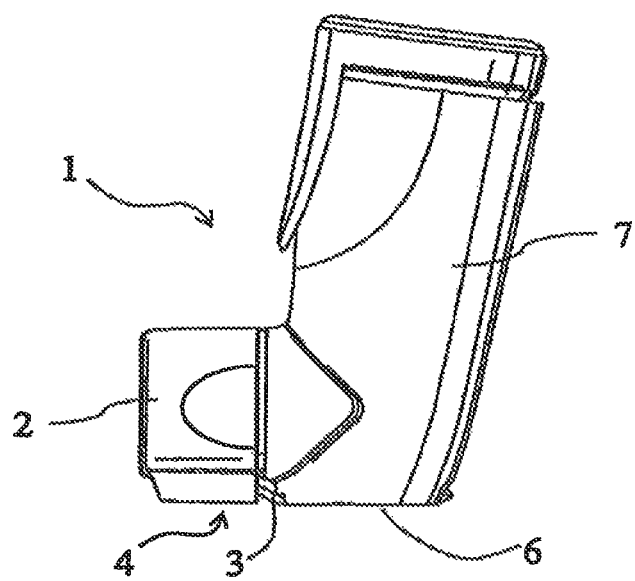
Figure 5:
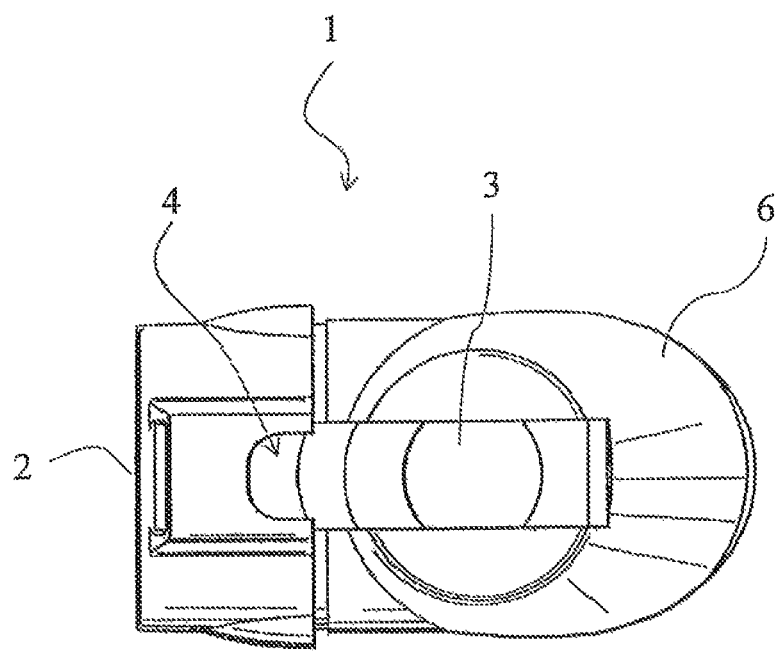

FIG. 4 shows a side view of a mouthpiece cap which can be incorporated into an inhaler according to a preferred form of the present invention, the cap is shown from the side and the cap is in the closed position in which it fits over the mouthpiece in order to occlude it; and FIG. 5 shows a bottom view of a preferred form of the invention in this view the cap is fitted over the mouthpiece overlying the portion of the mouthpiece which projects form the main body of the inhaler and occluding the opening of the mouthpiece through which the medicament exits the inhaler.

Various forms of inhalers (1) are known, one subset of these inhalers provide a dose of medicament from a canister in which the medicament is stored under pressure along with a suitable propellant. In such inhalers the medicament exits via a mouthpiece through which a user inhales. The medicament often exits from a nozzle in the mouthpiece and said nozzles are often small and thus easily blocked by such things as dirt and dust. For this reason known forms of inhaler often include a cap which can be placed into or over the mouthpiece in order to block it and prevent the egress of such dirt and dust. These caps may be misplaced if they are separate from the mouthpiece or main body of the inhaler thus defeating their purpose. Known forms of inhalers (1) provide an attachment of the cap to the mouthpiece or main body of the inhaler by means of a strap or string. Known forms of strap are made from rubber or a similar material but this may involve manufacturing difficulties as, for various reasons, the main body of inhalers are often made of plastic. At least one additional manufacturing step must be provided adding to cost.

A problem exists in trying to make sure that any attachment strap closely underlies or follows the contours of parts of the inhaler near the nozzle when the material of the strap is plastic without sufficient elastic flexibility to stretch so as to pull tight against the inhaler.

In a preferred form of the present invention the cap (2) is attached in a sliding arrangement (4) to the strap (3). It thus can slide back a forth between stops. The amount of movement possible should be sufficient to enable the cap (2) to rest in a position in which it fully covers the nozzle (5) hut allow it to slide away from the body (7) so as to allow the strap to pivot down away from the base (6) of the main body (7) of the inhaler (1). In preferred forms of the invention the strap (3) can be pivoted (8) so that it can overlie or abut the rear of the main body (7) of the inhaler. In the most preferred form of the invention the strap does not follow the contour of the rear wall of the main body. However in other forms of the invention the rear wall could have an indentation (10), which could allow the strap to rest and even perhaps lock therein. This could keep the strap (3) and the cap (2) also completely away from the nozzle (5) and thereby ensure that the user may freely inhale even if they have not positioned their hands to hold the strap and cap out of the way.

In forms of the invention the sliding attachment (4) of the cap (2) to the strap (3) may be such that they cannot be detached without destroying one or other of them. In other forms it may be possible to detach them by, for example, applying pressure to the lug (11). It is not expected that the user will have any cause to remove or replace the cap (2). However this may provide means whereby the user can remove the cap (2) and obtain a dose in an emergency when the cap (2) is damaged in such a manner to prevent it from being used in the usual manner. This may be an additional advantage of an alternative form of the present invention.

Those skilled in the art to which the invention relates will see that the present invention can be utilised in a number of different inhalers. The inhaler may include a dose or actuation counter to provide an indication of the number of doses dispensed from the canister or, as the number of doses present in a canister when it is hill is known, the number of does remaining in the canister and hence the inhaler. This is important information as it allows to user to ensure that they have sufficient doses remaining in their inhaler and when they should obtain a canister refill or a replacement inhaler.

Inhalers are sometimes coloured so as to indicate the medicament contained therein or the company, which manufactures the inhaler. Different number of doses within an inhaler could also be indicated buy various colour schemes. Thereby it is useful for the strap and the main body of the inhaler to be manufactured from the same material. In other less preferred forms of the invention the strap could be of the same material of the base of the main body of the inhaler. The strap and base of the main body of the inhaler could then be co-moulded onto the remainder of the main body.

The present invention provides an inhaler having an integrated strap, which attaches a cap to the inhaler body.

Accordingly in a first aspect the present invention consists of an inhaler (1) for dispensing doses of medicament from a container under user activation said inhaling comprising a body (7) including a mouthpiece (5) through which said medicament is dispensed and a cap (2) which can be place in a position to substantially occlude said mouthpiece (5) where said cap (2) is attached to said body (7) by a strap (3) which pivots from said body (7), said cap (2) being arranged to slide on said strap (3) such that said cap (2) must translate away from said mouthpiece (5) prior to the pivoting of said strap (3).

Preferably said mouthpiece (5) projects from said body (7);

Preferably said mouthpiece (5) is substantially oval in cross section.

Preferably said cap (2) both occludes said mouthpiece (5) and overlies the projection of said mouthpiece (5).

Preferably said inhaler (5) is a plastic material with said strap and said body moulded as a unit.

Preferably said strap (3) underlies said body and substantially follows the contours thereof (10).

The figures also show how the inhaler can be assembled. The main body (7) of the inhaler (1) is oriented so that the strap underlies the base of the main body (7), The mouthpiece nozzle (5) is inserted into the cap (2) and the combined cap (2) and nozzle (5) oriented so that the lug (11), which attaches the cap to the strap, is aligned with the strap. The combined cap and nozzle and the main body of the inhaler is then pushed together. The lug 1) causes the cap to be attached to the strap (3) and thus the rest of the inhaler. The abovementioned steps are, of course, best automated and various testing stages or steps can be included in the process. These steps may include checks to ensure that parts are s correctly arranged in relation to one another. Tests may also check the functionality of the parts and any assembled subassemblies.

Finally, it will be understood by a person skilled in the art that the present invention is not limited to the described embodiment but can be modified in many different ways within the scope of the appended claims.

I claim:

1. An inhaler comprising:
   a body including a mouthpiece and a base having a groove; and
   a cap coupled to the body by a strap, wherein the strap is positioned within the groove when the cap engages the mouthpiece, wherein the cap is configured to translate towards and away from the mouthpiece, wherein the strap includes a first section along which the cap configured to translate towards and away from the mouthpiece, a second section for positioning within the groove of base, and a third section between the first section and the second section, wherein, when the cap engages the mouthpiece, the third section of the strap extend at an angle from the first section to the second section, and wherein the cap includes an opening for receiving the strap as the cap translates towards the mouthpiece.

2. The inhaler of claim 1, wherein the cap is configured to slide along the first section of the strap.

3. The inhaler of claim 1, wherein the cap is configured to occlude the mouthpiece.

4. The inhaler of claim 1, wherein the second section of the strap is configured to pivot relative to the body.

5. The inhaler of claim 4, wherein the second section of the strap is configured to pivot away from the body after the cap translates away from the mouthpiece.

6. The inhaler of claim 1, wherein the cap includes a lug configured to couple the cap to the strap.

7. An inhaler comprising:
   a body including a mouthpiece and a base having a groove; and
   a cap coupled to the body by a strap, wherein the strap is positioned within the groove when the cap engages the mouthpiece, wherein the cap is configured to translate towards and away from the mouthpiece by sliding along the strap, wherein the strap includes a first section along which the cap is configured to slide, a second section for positioning within the groove of the base, and a third section between the first section and the second section, wherein when the cap engages the mouthpiece, the third section of the strap extends at an angle from the first section to the second section, and wherein the strap is formed of a non-elastic material.

8. The inhaler of claim 7, wherein the strap is formed of a rigid material.

9. The inhaler of claim 7, wherein the first section of the strap includes a channel, and the cap includes a lug, and wherein the lug is configured to slide along the channel.

10. The inhaler of claim 9, wherein the channel includes a first stop and a second stop, and wherein the lug is configured to slide along the channel between the first stop and the second stop.

11. The inhaler of claim 7, wherein the second section of the strap underlies the base of the body when the cap engages the mouthpiece.

12. An inhaler comprising:
   a body including a mouthpiece and a base; and
   a cap coupled to the body by a strap, wherein the strap underlies the base of the body, wherein the base of the body includes a groove, and the strap is positioned within the groove when underlying the base, wherein the strap is positioned outside the groove when the cap is disengaged from the mouthpiece, wherein the strap includes a first section along which the cap is configured to slide, a second section for positioning within the groove of the base, and a third section between the first section and the second section, wherein, when the cap engages the mouthpiece, the third section of the strap extends at an angle from the first section to the second section, and wherein the cap is configured to translate towards and away from the mouthpiece by sliding along the strap.

13. The inhaler of claim 12, wherein the mouthpiece is positioned on a first side of the body, and the strap is coupled to the body on a second side of the body opposite the first side.

14. The inhaler of claim 13, wherein the second section of the strap is configured to pivot relative to the body at the second side of the body.

15. The inhaler of claim 12, wherein, when the second section of the strap is positioned within the groove, the strap and the base form a substantially flat surface to allow the inhaler to stand upright when the base is placed on a support surface.

16. The inhaler of claim 12, wherein the cap includes at least one projection for gripping by a user.

17. The inhaler of claim 16, wherein the at least one projection extends laterally beyond the body.

* * * * *